United States Patent
Lewerenz

(10) Patent No.: US 12,041,961 B2
(45) Date of Patent: Jul. 23, 2024

(54) METHOD OF MANUFACTURING A FILLING MATERIAL FOR A POUCHED SMOKELESS SNUS PRODUCT AND FILLING MATERIAL MANUFACTURED THEREFROM

(71) Applicant: Reemtsma Cigarettenfabriken GmbH, Hamburg (DE)

(72) Inventor: Nathalie Lewerenz, Hamburg (DE)

(73) Assignee: Reemtsma Cigarettenfabriken GmbM, Hamburg (DE)

( * ) Notice: Subject to any disclaimer, the term of this patent is extended or adjusted under 35 U.S.C. 154(b) by 13 days.

(21) Appl. No.: 16/754,251

(22) PCT Filed: Nov. 28, 2018

(86) PCT No.: PCT/EP2018/082759
§ 371 (c)(1),
(2) Date: Apr. 7, 2020

(87) PCT Pub. No.: WO2019/105960
PCT Pub. Date: Jun. 6, 2019

(65) Prior Publication Data
US 2020/0275689 A1    Sep. 3, 2020

(30) Foreign Application Priority Data
Nov. 29, 2017   (EP) .................................. 17204440

(51) Int. Cl.
*A24B 15/18* (2006.01)
*A24B 13/00* (2006.01)
(Continued)

(52) U.S. Cl.
CPC ............ *A24B 15/186* (2013.01); *A24B 13/00* (2013.01); *A24B 15/16* (2013.01); *A24B 15/385* (2013.01)

(58) Field of Classification Search
CPC ....... A24B 15/16; A24B 15/42; A24B 15/186; A24B 13/00; A24B 15/385
See application file for complete search history.

(56) References Cited

U.S. PATENT DOCUMENTS

2004/0123873 A1* 7/2004 Calandro ............... A24B 15/16
 131/359
2008/0029110 A1* 2/2008 Dube .................... A24B 13/00
 131/275

(Continued)

FOREIGN PATENT DOCUMENTS

EA  200702372 A1  6/2008
RU  2469625 C2  12/2012

(Continued)

OTHER PUBLICATIONS

Liquid Nicotine Wholesalers, https://liquidnicotinewholesalers.com/100mg-nicotine-liquid.html, accessed Nov. 22, 2022. Available on the web as early as Mar. 2016. (Year: 2016).*

(Continued)

*Primary Examiner* — Michael H. Wilson
*Assistant Examiner* — Stephanie Lynn Moore
(74) *Attorney, Agent, or Firm* — Fox Rothschild LLP

(57) ABSTRACT

The present invention is directed to a method of manufacturing a filling material for a pouched smokeless snus product, the method comprising the steps of: a) coating non-tobacco plant material with nicotine; b) mixing the coated non-tobacco plant material with further ingredients and optionally tobacco material to form the filling material; and c) optionally subjecting the filling material to a pasteurization step; as well as to products of such method.

16 Claims, 1 Drawing Sheet

(51) Int. Cl.
*A24B 15/16* (2020.01)
*A24B 15/38* (2006.01)

(56) References Cited

U.S. PATENT DOCUMENTS

| | | | |
|---|---|---|---|
| 2009/0293895 A1 | 12/2009 | Axelsson et al. | |
| 2011/0214681 A1* | 9/2011 | Axelsson | A61K 9/009 |
| | | | 131/369 |
| 2013/0118512 A1* | 5/2013 | Jackson | A24B 15/30 |
| | | | 131/355 |
| 2015/0024012 A1* | 1/2015 | Grossman | A61K 9/0092 |
| | | | 514/343 |
| 2015/0230516 A1 | 8/2015 | Stewart | |

FOREIGN PATENT DOCUMENTS

| WO | 2004/056363 A2 | 7/2004 |
|---|---|---|
| WO | 2010/031552 A1 | 3/2010 |
| WO | 2013/122948 A1 | 8/2013 |
| WO | 2015/009913 A1 | 1/2015 |
| WO | 2015198067 A1 | 12/2015 |
| WO | 2017/093488 A1 | 6/2017 |

OTHER PUBLICATIONS

International Search Report mailed on Feb. 26, 2019 in PCT Application No. PCT/EP2018/082759.
Extended European Search Report mailed on Jul. 6, 2018 in European Application No. 17204440.6-1105.
Office Action issued in corresponding application No. RU 2020112443/03 on Mar. 31, 2022.
Office Action mailed in corresponding JP Application No. 2020-527965 on Nov. 21, 2022.
Office Action issued in corresponding application No. BY 20200103 dated Oct. 25, 2022.

* cited by examiner

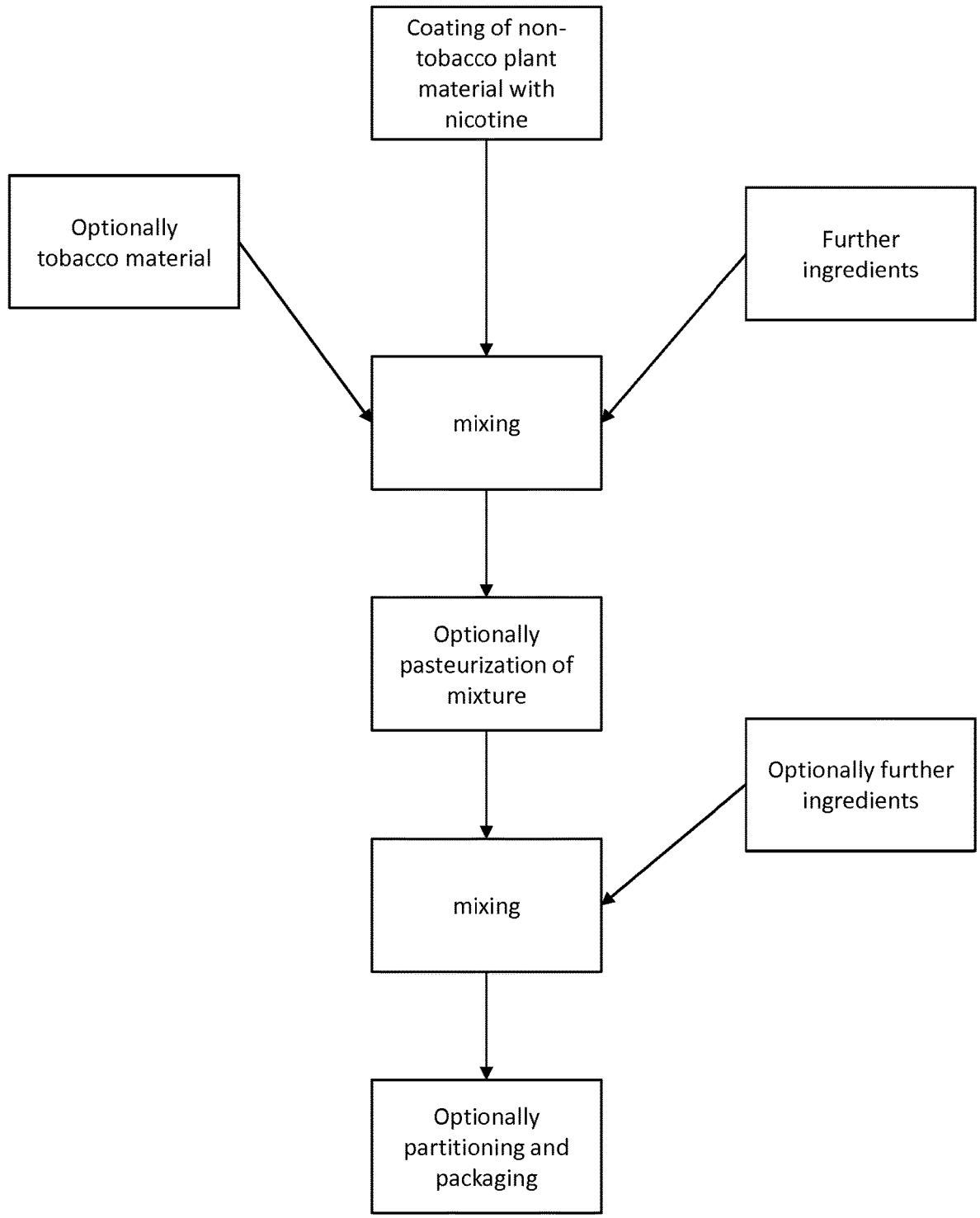

METHOD OF MANUFACTURING A FILLING MATERIAL FOR A POUCHED SMOKELESS SNUS PRODUCT AND FILLING MATERIAL MANUFACTURED THEREFROM

CROSS-REFERENCE TO RELATED APPLICATIONS

This application is a § 371 national phase entry of International Patent Application No. PCT/EP2018/082759, filed on Nov. 28, 2018, which claims priority to and the benefit of European Patent Application No. 17204440.6, filed on Nov. 29, 2017, both of which are hereby incorporated herein by reference in their entireties.

Consumption of smokeless tobacco-based products, like e.g. pouched smokeless tobacco products for oral consumption (e.g. snus or moist snuff), is common in societies. However, the use of tobacco material in such products limits the organoleptic properties of these products. The tobacco material has a typical colour, texture, smell and taste which may not always be attractive to the consumer. Further, tobacco material comprises constituents which may not be desirable in a pouched smokeless snus product.

Consequently, there is a need for a filling material for pouched smokeless snus products which allows for the provision of a nicotine content in a predetermined amount, while offering widespread opportunities to influence the organoleptic properties of the product.

The present invention provides a method of manufacturing a filling material for a pouched smokeless snus product. The method of the present invention comprises the steps of:
a) coating non-tobacco plant material with nicotine;
b) mixing the coated non-tobacco plant material with further ingredients and optionally tobacco material to form the filling material;
c) optionally subjecting the filling material to a pasteurization step; and
d) optionally mixing the product of step b) or c) with further ingredients.

This method allows the production of a filling material for a pouched smokeless snus product with unique organoleptic properties which may differ substantially from common fillings based predominantly on tobacco material while ensuring that the filling material encompasses nicotine in a pre-determined amount. By partially and/or completely replacing the tobacco part of the filling with non-tobacco plant material which has been pre-treated to be coated with nicotine, it is possible to provide a nicotine containing filling with a taste, smell, touch, sight and/or other organoleptic properties that cannot be achieved with common tobacco-based fillings. For example, the method of the present invention allows the manufacturing of a filling for a pouched smokeless snus product with a whitened appearance while maintaining a desired nicotine content without the need to use bleached or whitened tobacco material.

In FIG. 1, a schematic representation of the method of the invention is provided.

In step a) non-tobacco plant material is provided and coated with nicotine using a liquid solution comprising nicotine. The product of step a) is non-tobacco plant material coated with nicotine. Said nicotine-coated non-tobacco plant material is subjected to step b).

In step b), the nicotine-coated non-tobacco plant material is mixed with further ingredients, like e.g. water and salt (e.g. NaCl), and optionally uncoated non-tobacco plant material and/or tobacco material to form the filling material.

In step c) of the method of the invention, the mixture of step b) may be subjected to pasteurization, i.e. to a heat treatment step well known in the art in the manufacturing of snus filling. Step c) is optional. In case it is not intended to perform step c), all further ingredients of the filling material may be mixed in one step and steps b) and d) may be performed simultaneously. In case it is intended to include step c) into the method of the invention, in step b) only part of all the further ingredients of the filling material may be mixed-in and remaining further ingredients of the filling material may be mixed-in in step d) after pasteurization of the method of the invention.

The present invention is directed to manufacturing of a filling material for a pouched smokeless snus product. Pouched smokeless snus products are products for oral use which comprise a filling material which is encompassed in a pouch made of pouch material wherein the pouch material ensures that during consumption the particulate parts of the filling predominantly stay within the pouch while saliva- or water-soluble parts of the filling are at least in part allowed to pass the pouch material. Such pouched smokeless snus products are consumed by placing the pouched product into the oral cavity, most commonly between the lower gum and lip or upper gum and lip. By contact with the saliva, constituents of the filling elute from the pouch and are consumed by the consumer.

In the method of the invention, non-tobacco plant material is used. The non-tobacco plant material according to the present invention is used in the form of plant fibres wherein the term "fibres" encompasses plant material that is in particulate form and which preferably but not necessarily has an average length that exceeds the average width of the particles of the plant material.

The non-tobacco material is derived from plants other than plants of the genus *Nicotiana*. The non-tobacco material may be derived from any part of such plants, e.g. leafs, stem, roots etc., or any combination of different parts of said plants. The non-tobacco plant material comprises or consists of plant material derived from one particular plant species or from a combination of different plant species, provided that none of these plant species represents a member of the genus *Nicotiana*.

The non-tobacco plant material preferably comprises or consists of fibres derived from natural sources. However, the fibres of non-tobacco plant material may be processed before use, such as washed, ground, cut, cured, aged, dried, fermented, chemically modified and/or otherwise.

Preferably, the non-tobacco plant material comprises or consists of wheat fibres, oat fibres, potato fibres, bamboo fibres, buckwheat fibres, barley fibres, microcrystalline cellulose and/or combinations thereof. More preferably, the non-tobacco plant material comprises or consists of wheat fibres, particularly preferably the non-tobacco plant material comprises or consists of gluten-free wheat fibres.

According to a first step of the method of the invention said non-tobacco plant material is coated with nicotine using a liquid solution comprising nicotine.

Preferably, the non-tobacco plant material is coated with nicotine using a liquid solution comprising nicotine and glycerol. More preferably, the non-tobacco plant material is coated with nicotine using a nicotine-in-glycerol solution. For the purpose of the present invention, the term "nicotine-in-glycerol solution" refers to a liquid solution wherein the combined content of nicotine and glycerol together make up at least 90 weight-% of the total weight of the nicotine-in-glycerol solution, preferably at least 95 weight-%, more preferably at least 99 weight-%. In the method of the invention, the non-tobacco plant material may be coated with nicotine using a nicotine-in-glycerol solution wherein the nicotine is present in a concentration of 2 to 20 weight-%, preferably of 5 to 15 weight-%, more preferably of 10 weight-%, based on the total weight of the nicotine-in-glycerol solution.

It has surprisingly been found that coating of non-tobacco plant material with nicotine is particularly effective and/or sustained if coating is performed using a nicotine-in-glycerol solution as defined above.

The person skilled in the art is well aware of methods suitable to coat non-tobacco plant material with nicotine using a nicotine-containing liquid solution. For example, in the method of the present invention the non-tobacco plant material can be coated with nicotine by applying the nicotine-containing liquid solution in a spray coating process or in a drum coating process.

In the method of the invention, the non-tobacco plant material is coated with nicotine in step a) such that the nicotine content in nicotine-coated non-tobacco plant material is within the range of 0.1 to 10 weight-%, preferably of 1 to 5 weight-%, more preferably of 2.5 to 4.5 weight-%, even more preferably of about 3.35 weight-%, wherein indications in weight-% are based on the dry weight of the nicotine-coated non-tobacco plant material.

As used herein, the term "dry weight" means the weight of the reference excluding the weight of water and possible also other substances that may evaporate from the reference during drying.

After the non-tobacco plant material has been coated with nicotine, in the method of the present invention the coated non-tobacco plant material is mixed with further ingredients to form the filling material. The term "further ingredient" as used herein refers to any substance other than nicotine-coated non-tobacco plant material and tobacco material. Such further ingredients preferably comprise one or more of water, non-tobacco plant material not coated with nicotine, stabilizers, humectants, plasticisers, thickeners, dyes, salts, flavours, gum base, flavour additives or any combination thereof. Exemplary embodiments of preferred further ingredients are water, NaCl, NH$_4$Cl, Na$_2$CO$_3$, propylene glycol, one or more flavours and/or combinations thereof In the method of the invention, the nicotine-coated non-tobacco plant material of step a) is mixed with further ingredients and optionally tobacco material such that the filling material formed comprises nicotine coated non-tobacco plant material in a concentration of 70 to 99 weight-%, preferably of 75 to 95 weight-%, more preferably of 80 to 90 weight-%, wherein indications in weight-% are based on the dry weight of the total filling material.

In step b) of the method of the invention, the nicotine-coated non-tobacco plant material of step a) is mixed with further ingredients and optionally tobacco material such that the filling material formed comprises a water content of 30 to 50 weight-%, preferably of 35 to 45 weight-%, based on the total weight of the filling material. As used herein, the term "water content" means the total water content in the filling material manufactured by the method of the invention as measured using a standardized method of water analysis, such as, Karl Fisher titration of gas chromatography (GC).

The present invention allows manufacturing of filling material for a pouched smokeless snus product that is either tobacco-free or which comprises tobacco material. In case the filling material is intended to be tobacco free, no tobacco material is mixed with the coated non-tobacco plant material. In case it is intended to provide filling material which comprises tobacco material, the coated non-tobacco plant material is mixed in step b) with appropriate tobacco material.

As used herein, the term "tobacco material" denotes any part of any member of a plant of the genus *Nicotiana* or material derived therefrom. The tobacco material may be whole, shredded, threshed, cut, ground, cured, fermented, processed, reconstituted or otherwise treated. The tobacco material may also be in the form of finished products, including any smokeless tobacco compositions that are orally consumed. The tobacco material used herein encompasses tobacco-containing snus e.g. produced according to the well known technology.

The tobacco material used in the method of the invention may be treated to achieve a desired colour effect or the like. Preferably, the tobacco material comprises or consists of tobacco material that has been bleached or whitened. Methods and procedures in order to prepare bleached or whitened tobacco material are known in the art and comprise the use of whiteners or bleaching agents. Alternatively or in addition, the tobacco material may be heat treated in order to arrive in a decrease of colouring agents. It is particularly preferred to prepare the whitened or bleached tobacco material by washing the tobacco material in hot water.

If the manufacturing of tobacco containing filling material is intended, in step b) of the method of the invention tobacco material is preferably mixed in such a way that a filling material is formed which comprises tobacco material in a concentration of 0 to 15 weight-%, preferably in a concentration of 0.1 to 10 weight-%, more preferably in a concentration of 2 to 8 weight-%, wherein indications in weight-% are based on the dry weight of the total filling material.

Optionally, the method of the invention further comprises step e), wherein in step e) the filling material is divided into individual portions (portioning) and the individual portions of the filling material are filled into separate pouches (packaging).

The present invention is also directed to a filling material for use in a pouched smokeless snus product, wherein said filling material is obtainable or obtained by a method of the present invention.

The filling material of the present invention preferably comprises or consists of:

| | | |
|---|---|---|
| 70 to 99 | weight-% | nicotine-coated non-tobacco plant material; |
| 0 to 15 | weight-% | tobacco material, preferably bleached tobacco material; and |
| 0 to 30 | weight-% | further ingredients; | wherein above mentioned indications in weight-% are based on dry weight of the total filling material;

wherein the nicotine-coated non-tobacco plant material has a nicotine content within the range of 0.1 to 10 weight-% based on the dry weight of the nicotine-coated non-tobacco plant material;

and wherein the filling material has a water content of 30 to 50 weight-% based on the total weight of the filling material.

Even more preferably, the filling material of the present invention comprises or consists of:

| | | |
|---|---|---|
| 70 to 99 | weight-% | nicotine-coated non-tobacco plant material; |
| 1 to 15 | weight-% | tobacco material, preferably bleached tobacco material; and |
| 1 to 30 | weight-% | further ingredients; | wherein above mentioned indications in weight-% are based on dry weight of the total filling material;

wherein the nicotine-coated non-tobacco plant material has a nicotine content within the range of 0.1 to 10 weight-% based on the dry weight of the nicotine-coated non-tobacco plant material;

and wherein the filling material has a water content of 30 to 50 weight-% based on the total weight of the filling material.

The present invention is also directed to a pouched smokeless snus product comprising the filling material of the present invention.

In the following, the present invention is illustrated by way of examples.

EXAMPLES

Example 1: Preparation of Nicotine-Coated Non-Tobacco Plant Material

In this Example, the non-tobacco plant material is coated with nicotine using a liquid nicotine-in-glycerol solution, wherein the nicotine-in-glycerol solution is sprayed on the non-tobacco plant material in a fluidized bed process. Alternatively, the non-tobacco plant material can be coated with nicotine using a liquid nicotine-in-glycerol solution in a drum coating process.

a) 600 g wheat fibres (WF 200 provided as VITACEL by J. Rettenmaier & Söhne GmbH & Co KG, DE) are spray coated with 350 g nicotine-in-glycerol solution (10 weight-% nicotine in glycerol, provided by Siegfried Ltd, CH) in a fluidized bed process.

The desired amount of nicotine-in-glycerol solution was successfully coated onto the wheat fibres to give a product of approx. 910 g of nicotine-coated wheat fibres with a nicotine content of approx. 3.8 weight-% based on the total weight of the nicotine-coated wheat fibres.

b) 600 g wheat fibres (WF 200 provided as VITACEL by J. Rettenmaier & Söhne GmbH & Co KG, DE) are spray coated with 264 g nicotine-in-glycerol solution (10 weight-% nicotine in glycerol, provided by Siegfried Ltd, CH) in a fluidized bed process.

The desired amount of nicotine-in-glycerol solution was successfully coated onto the wheat fibres to give a product of approx. 870 g of nicotine-coated wheat fibres with a nicotine content of approx. 3.0 weight-% based on the total weight of the nicotine-coated wheat fibres.

c) 600 g wheat fibres (WF 200 provided as VITACEL by J. Rettenmaier & Söhne GmbH & Co KG, DE) are spray coated with 450 g nicotine-in-glycerol solution (10 weight-% nicotine in glycerol, provided by Siegfried Ltd, CH) in a fluidized bed process.

The desired amount of nicotine-in-glycerol solution was successfully coated onto the wheat fibres to give a product of approx. 1043 g of nicotine-coated wheat fibres with a nicotine content of approx. 4.3 weight-% based on the total weight of the nicotine-coated wheat fibres.

Example 2: Formation of Filling Material for Use in a Pouched Smokeless Snus Product Basically, the method of the invention is based on mixing nicotine-coated non-tobacco plant material with further ingredients and optionally tobacco material in order to form a filling material suitable for use in a pouched smokeless snus product. The method can be performed in various ways, e.g. with or without a pasteurization step.

a) Method without a Pasteurization Step

An exemplary method for producing a batch of a filling material for use in a pouched smokeless snus product comprises the step of mixing the following ingredients:

| | |
|---|---|
| 135 kg | nicotine-coated wheat fibres of Example 1 a), b) or c); |
| 6.5 kg | tobacco material, preferably whitened or bleached tobacco material, e.g. tobacco material whitened by washing with hot water; |
| 78 kg | water; |
| 10.4 kg | NaCl; |
| 12.06 kg | ammonium chloride (20%); |
| 1.18 kg | sodium carbonate; |
| 5.6 kg | propylene glycol; and |
| | optionally flavour. |

All ingredients are added in a single vessel and mixed. The resulting filling material may be partitioned and packaged into pouched smokeless snus products.

b) Method with a Pasteurization Step

An exemplary method for producing a batch of a filling material for use in a pouched smokeless snus product comprises the step of mixing the following ingredients:

| | |
|---|---|
| 135 kg | nicotine-coated wheat fibres of Example 1 a), b) or c); |
| 6.5 kg | tobacco material, preferably whitened or bleached tobacco material, e.g. tobacco material whitened by washing with hot water; |
| 78 kg | water; and |
| 10.4 kg | NaCl. |

The mixture is subjected to a pasteurization step. Said pasteurization step is similar to the pasteurization step used in the preparation of classical smokeless tobacco snus according to standard processes.

The pasteurized mixture is further subjected with the following further ingredients:

| | |
|---|---|
| 12.06 kg | ammonium chloride (20%); |
| 1.18 kg | sodium carbonate; |
| 5.6 kg | propylene glycol; and |
| | optionally flavour. |

All ingredients are added in a single vessel and mixed. The resulting filling material may be partitioned and packaged into pouched smokeless snus products.

Example 3: Formation of Tobacco-Free Filling Material for Use in a Pouched Smokeless Snus Product Basically, the method of the invention is based on mixing nicotine-coated non-tobacco plant material with further ingredients in order to form a tobacco-free filling material suitable for use in a pouched smokeless snus product. The method can be performed in various ways, e.g. with or without a pasteurization step.

a) Method without a Pasteurization Step

An exemplary method for producing a batch of a filling material for use in a pouched smokeless snus product comprises the step of mixing the following ingredients:

| | |
|---|---|
| 135 kg | nicotine-coated wheat fibres of Example 1 a), b) or c); |
| 118 kg | water; |
| 13.75 kg | NaCl; |

-continued

| | |
|---|---|
| 5.98 kg | ammonium chloride (20%); |
| 2.3 kg | sodium carbonate; |
| 12.34 kg | propylene glycol; and |
| | optionally flavour. |

All ingredients are added in a single vessel and mixed. The resulting filling material may be partitioned and packaged into pouched smokeless snus products.

b) Method with a Pasteurization Step

An exemplary method for producing a batch of a tobacco-free filling material for use in a pouched smokeless snus product comprises the step of mixing the following ingredients:

| | |
|---|---|
| 135 kg | nicotine-coated wheat fibres of Example 1 a), b) or c); |
| 118 kg | water; and |
| 13.75 kg | NaCl. |

The mixture is subjected to a pasteurization step. Said pasteurization step is similar to the pasteurization step used in the preparation of classical smokeless tobacco snus according to standard technology.

The pasteurized mixture is further subjected with the following further ingredients:

| | |
|---|---|
| 5.98 kg | ammonium chloride (20%); |
| 2.3 kg | sodium carbonate; |
| 12.34 kg | propylene glycol; and |
| | optionally flavour. |

All ingredients are added in a single vessel and mixed. The resulting filling material may be partitioned and packaged into pouched smokeless snus products.

The invention claimed is:

1. A method of manufacturing a filling material for a pouched smokeless snus product, the method comprising the steps of:
   a) coating non-tobacco plant material with nicotine using a liquid nicotine-in-glycerol solution, wherein the nicotine-in-glycerol solution comprises the nicotine in a concentration of 2 to 20 weight-% based on the total weight of the nicotine-in-glycerol solution, and wherein the combined content of nicotine and glycerol together make up at least 90 weight-% of the total weight of the nicotine-in-glycerol solution;
   b) mixing the coated non-tobacco plant material with water and salt and optionally uncoated non-tobacco plant material and/or tobacco material to form the filling material;
   c) optionally subjecting the filling material to a pasteurization step; and
   d) optionally mixing the product of step b) or c) with further ingredients.

2. The method of claim 1, wherein in step b) the salt is NaCl.

3. The method according to claim 1, wherein the non-tobacco plant material is coated with nicotine using a spray coating process or a drum coating process.

4. The method according to claim 1, wherein the non-tobacco plant material comprises fibres or particles from non-tobacco plants.

5. The method according to claim 1, wherein in step b) tobacco material is mixed in to form a filling material comprising tobacco material in a concentration of 0 to 15 weight-%, wherein indications in weight-% are based on the dry weight of the total filling material.

6. The method according to claim 1, wherein the tobacco material is bleached.

7. The method according to claim 1, wherein the filling material comprises a water content of 30 to 50 weight-% based on the total weight of the filling material.

8. The method according to claim 1, wherein the filling material comprises coated non-tobacco plant material of step a) in a concentration of 70 to 99 weight-%, wherein the indications in weight-% are based on the dry weight of the total filling material.

9. The method according to claim 1, wherein the nicotine-coated non-tobacco plant material of step a) has a nicotine content within the range of 0.1 to 10 weight-%, wherein the indications in weight-% are based on the dry weight of the nicotine-coated non-tobacco plant material.

10. The method according to claim 1, wherein the further ingredients of the filling material of step b) and/or d) comprise water, non-tobacco plant material not coated with nicotine, stabilizers, humectants, plasticisers, thickeners, dyes, salts, flavours, gum base, flavour additives or any combination thereof.

11. The method according to claim 1, wherein the method comprises the further step:
    e) portioning the filing material into individual portions and packaging individual portions into separate pouches.

12. A filling material for use in a pouched smokeless snus product, the filling material being manufactured by a method according to claim 1.

13. The filling material of claim 12, wherein the filling material comprises:
    70 to 99 weight-% nicotine-coated non-tobacco plant material;
    0 to 15 weight-% tobacco material; and
    0 to 30 weight-% further ingredients;
    wherein above mentioned indications in weight-% are based on dry weight of the total filling material;
    wherein the nicotine-coated non-tobacco plant material has a nicotine content within the range of 0.1 to 10 weight-% based on the dry weight of the nicotine-coated non-tobacco plant material;
    and wherein the filling material has a water content of 30 to 50 weight-% based on the total weight of the filling material.

14. A pouched smokeless snus product comprising a filling material of claim 12.

15. The method according to claim 1, wherein in step d) the further ingredients comprise $NH_4Cl$, $Na_2CO_3$, propylene glycol, optionally one or more flavours and/or combinations thereof.

16. The method according to claim 1, wherein the non-tobacco plant material comprises wheat fibres, oat fibres, potato fibres, bamboo fibres, buckwheat fibres, barley fibres, microcrystalline cellulose and/or combinations thereof.

* * * * *